US00PP35354P3

(12) United States Plant Patent
Shipley et al.

(10) Patent No.: US PP35,354 P3
(45) Date of Patent: Aug. 29, 2023

(54) ***LEUCOPHYLLUM* HYBRID PLANT NAMED 'PURPLE RAIN'**

(50) Latin Name: ***Leucophyllum frutescens* X *laevigatum***
Varietal Denomination: Purple Rain

(71) Applicants: Nicholas Benoit Shipley, Tucson, AZ (US); Russ A Buhrow, Tucson, AZ (US)

(72) Inventors: Nicholas Benoit Shipley, Tucson, AZ (US); Russ A Buhrow, Tucson, AZ (US)

( * ) Notice: Subject to any disclaimer, the term of this patent is extended or adjusted under 35 U.S.C. 154(b) by 0 days.

(21) Appl. No.: 17/300,793

(22) Filed: Nov. 12, 2021

(65) Prior Publication Data

US 2023/0200272 P1 Jun. 22, 2023

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson

(57) ABSTRACT

A new and distinct *Leucophyllum frutescens* X *laevigatum* plant named 'Purple Rain' is characterized by its broad, dense growth form, pleasantly fragrant lavender flowers, dark green leaves, fast growth and superior resistance to damping off diseases both in the nursery and in the landscape.

2 Drawing Sheets

Latin name: *Leucophyllum frutescens* X *laevigatum* 'Purple Rain'.

Varietal denomination: 'Purple Rain'.

BACKGROUND OF THE INVENTION

The present invention relates to a new and distinct cultivar of *Leucophyllum*. The cultivar originated from an ongoing *Leucophyllum* breeding program. *Leucophyllum frutescens* 'Green Cloud' (not patented) was used as the female parent, while the male parent was from a proprietary breeding line of *Leucophyllum laevigatum*. The $F_1$ generation resulting from this cross was highly variable as the parental plants were apparently quite heterozygous. One plant stood out from the rest because of it's fast nursery growth, dense growth habit, dark green leaves, fragrant lavender colored flowers and excellent resistance to damping off diseases and is the object of this application. This plant looks superficially like *Leucophyllum* hybrid 'Heavenly Cloud' (not patented) with similar flower and leaf color, but with improved growth form and disease resistance, providing a plant with lower maintenance costs and improved survival both in the grower nursery and in the landscape.

SUMMARY OF THE INVENTION

Among the features that distinguish the new *Leucophyllum* cultivar from all other available and commercial varieties of *Leucophyllum* known to the inventor are the following combination of characteristics: evergreen shrub with dark green leaves, considerably broader than tall with a dense, arching growth form, pleasantly fragrant lavender flowers which last 3 days each and possessing superior resistance to damping off diseases both in the nursery and in the landscape. The propagation procedure is as follows: Semihardwood cuttings 4-5" long are prepared by removing the lower leaves, then dipping the cleared portion of the cut into a 1:10 solution of DIP'N GROW™. The cuttings are then inserted about one inch into prepared peat trays. The trays are moved to a mist house with mist applied every 20 minutes and temperature maintained between 70-85° F. Rooting is generally complete within 4 weeks.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Leucophyllum* hybrid 'Purple Rain' growing near Sahuarita, Ariz., depicted in color as nearly correct as it is possible to make in a color illustration of the character.

DETAILED PLANT DESCRIPTION

Figure 1:
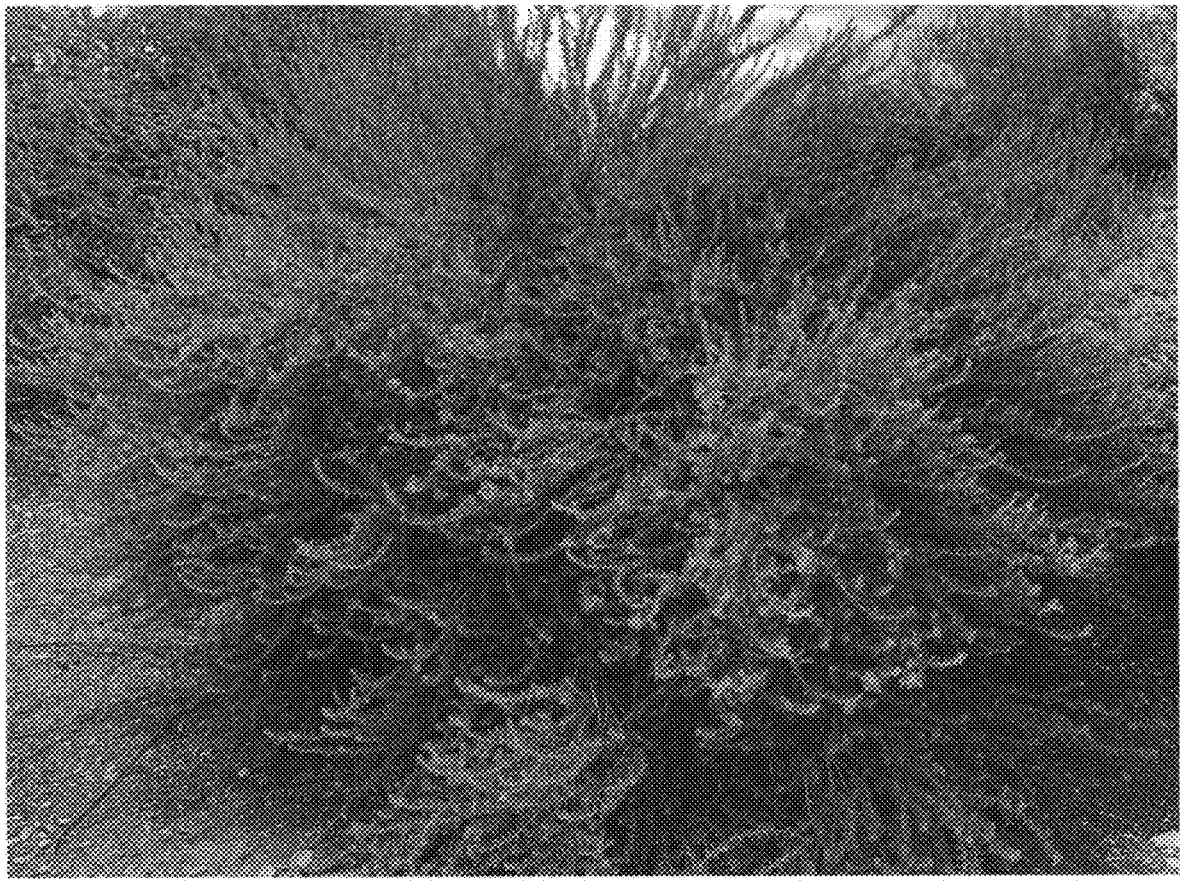
FIG. 1 shows *Leucophyllum* hybrid 'Purple Rain' growing in the ground at a commercial nursery near Sahuarita, Ariz. aged 6 years.
Figure 2:
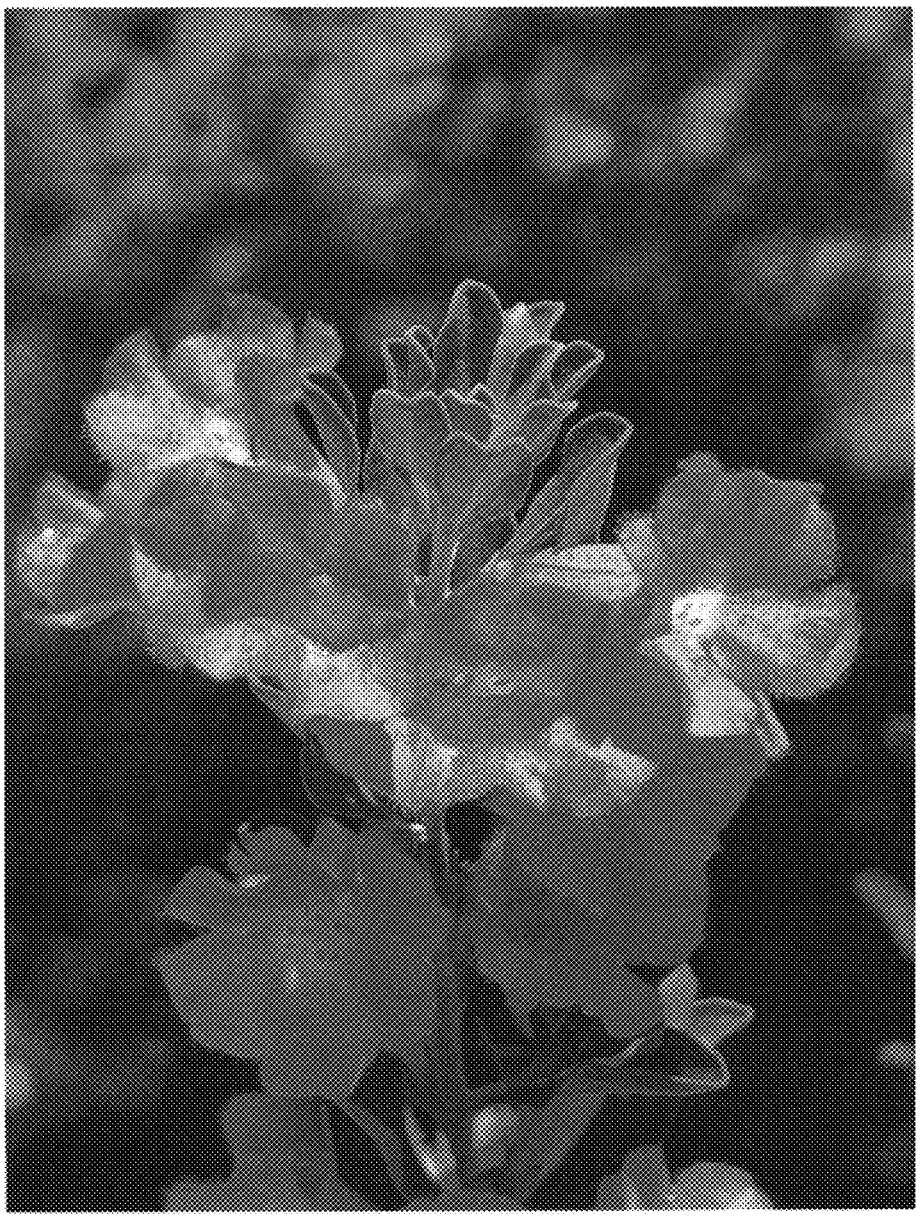
FIG. 2 is a closeup of the leaves and flowers of *Leucophyllum* hybrid 'Purple Rain'.

The following is a detailed description of the new *Leucophyllum* plant based upon the original plant growing in the ground near Sahuarita, Ariz. at age 6 years and plants grown from cuttings growing in #5 pots aged 4-5 months from rooting.

The color descriptions are based upon the $5^{th}$ edition R.H.S. Colour Chart, copyright 2007. Color names other than common usage are as listed in *COLOR Universal Language and Dictionary of Names*, by Kenneth L. Kelly and Deane B. Judd; National Bureau of Standards special publication 440. Washington, D.C.: U.S. Department of Commerce, National Bureau of Standards, December 1976.

'Purple Rain' is a much branched flowering evergreen shrub measuring 9 feet tall×13 feet wide unpruned at age 6 years growing in good soil at a commercial nursery near Sahuarita, Ariz. with adequate irrigation and fertilization. This shrub has a dense, arching branch arrangement.

Flowers are showy and pleasantly fragrant and are produced throughout the warm season (generally from late April through October in this area), particularly during rainy periods.

Young mature stems are terete, 1-2 mm in diameter, colored 194A, very finely puberulent with stellate hairs, these visible at 20×. The leaf arrangement is alternate. Internodes measure between 1-18 mm in length. Branch angles vary from about 30-60 degrees.

Older stems measuring from 1.2-4.0 mm in diameter grade gradually from color 194A at the younger portions to 199A on the older, thicker parts.

Leaves are sessile, without stipules, and oblanceolate in shape, slightly twisted and somewhat coriaceous. The apex is rounded to slightly apiculate. The base is long attenuate. Leaves measure 12-32 mm long×5-11 mm wide×0.5 mm thick.

The leaf adaxial surface is glabrate with scattered short, straight hairs visible under 20×. Color is 138A. The leaf midrib is depressed, but otherwise like the rest of the adaxial surface. Secondary veins are not visible.

The leaf abaxial surface is glabrate with scattered straight and stellate hairs visible at 20×. Color is 138A. The midrib is raised, hemicylindrical, color 138B, puberulent with very fine stellate hairs visible at 20×. Secondary veins are not visible.

Mature buds are long obovate, measuring 12-13 mm long×4-5 mm high×3-4 mm wide. The bud, viewed from the apex is weakly 5 angled near the petal lobes, and is shorter on the ventral side than the dorsal portion at about a 60 degree angle. The 5 petal lobes are overlapping, the upper 2 enclosing the lower 3. The petal lobe margins are ciliate with straight hairs colored 77A. Bud color is 77B except on the underside of the throat which is colored 159C and spotted with round 164C spots measuring around 0.5 mm.

Flowers are axillary, single and alternate in the leaf axils. Flowers are mildly and pleasantly fragrant, lasting about 3 days, the corollas falling away about a week later.

Pedicels measure 3.0 mm long×0.8 mm in diameter, terete and puberulent with fine, stellate hairs, more densely so at the flower end. Pedicels are colored 191B with hairs colored NN155C.

Calyx is 5 lobed, the lobes lanceolate, fused to the calyx tube below. The calyx lobes are mostly appressed to the corolla, sometimes slightly spreading at the apices. Calyx measures 5.5 mm long×4.5 mm wide. The lobes measure 3 mm long×1.5 mm wide at the lobe base. The lobe apex is acute, margins entire. The calyx (color 191B) is externally finely puberulent with stellate hairs, these colored NN155C. The calyx base is rounded, 1 mm long×2.5 mm in diameter. The calyx tube between the calyx base and the calyx lobes is 1.5 mm in length. The calyx interior is glabrous, colored between 135B and 135C.

Flowers are trumpet shaped, 5 lobed and shorter in length at the upper 2 lobes than at the lower 3 lobes. Flowers measure 22-26 mm long×18-26 mm wide×12-22 mm high. The exterior of the corolla including the petal lobes is colored 80D except the lower half of the tube, which is colored NN155C spotted with 76B.

The interior petal lobes are colored N78C which abruptly changes to N78D at the upper throat. The interior lower half of the tube is colored N155D spotted with 163B.

Corolla is externally glabrous except for ciliate at the petal lobe margins, hairs colored 77A.

The petal lobe interiors are pubescent with hairs identical to petal lobe margin hairs in color and type. These hairs terminate abruptly at the base of the 2 upper petal lobes, but near the bottom of the lower petal lobes the hairs become longer and glandular. The hairs at that point become white (NN155D) and thin, not glandular. This white beard terminates rather abruptly at about the height of the anthers. The lower tube is glabrous below that. The petal lobes are orbicular in shape and slightly crisped, the lower lobes more so than the upper. The upper lobes measure 7 mm long×7 mm wide. the lower lobes measure 8-9 mm long×8 mm wide.

Stamens number 4 of 2 different lengths with the upper 2 longer than the lower 2. A staminode is absent. The stamens are attached to the corolla near its base.

Upper stamens measure 10-11 mm long. The filaments are terete, basally color N155B, glabrous, gradually tapering from 0.75 mm diameter at the base to 0.4 mm near the anther attachment. The upper ⅔ of the filament gradually fades in color to NN155C. Anthers are explanate, measuring 1.5 mm long×0.6 mm wide×0.25 mm thick, color 164D. Pollen is abundant, color 164D.

Lower (short) stamens measure 8 mm long, the filament base 0.6 mm diameter and below the anther 0.3 mm. Anther measures 1.0 mm long×0.5 mm wide×0.2 mm thick. Colors are the same as the long stamens.

The pistil measures 14 mm long×1.2 mm wide (at the ovary). The base of the pistil is highly nectiferous. Ovary is superior, ovoid in shape measuring 2.0 mm long×1.2 mm in diameter. Ovary consists of 2 carpels, is glabrous, color 145D. Style is basally terete, 0.5 mm diameter, becoming flattened and spatulate the ultimate 2 mm. The glabrous style is colored 201C next to the ovary, grading to 77D at the stigma attachment. The stigma is thickened and crescent shaped following the margin of the spatulate portion of the style. The stigma surface is verrucate and colored 77D. The fruit at maturity but not ripe is a roughly ovoid, hard, 2 carpeled capsule measuring 6.0 mm long×3.5 mm high×2.7 mm wide. The glabrous surface is waxy, colored 146A. A furrow runs the length of both sides of the fruit following the carpel wall. The fruit contains about 20 seeds.

The ripe fruit, colored N199B dehisces along 4 lines apically. The seeds are irregular from compression within the fruit and measure about 1 mm in size, color N199C.

*Leucophyllums* are generally insect pest and disease free except for the Texas (Cotton) Root Rot fungus *Phymatotrichum omnivorum* and sudden death in commercial nurseries from damping off.

In heavier soils, especially if the soil becomes waterlogged, damping off can also occur in the landscape. Cultivation of "Rangers" is limited on the eastern margin of the temperature adaptation zone by death because of excessive moisture. Several cultivars including 'Green Cloud' and 'Compacta' are known to have greater than average resistance to damping off diseases. Several cultivars are so sensitive to damping off that they are not economic to produce and are rarely available in the trade. *Leucophyllum* hybrid 'Purple Rain' has demonstrated superior resistance to damping off in the nursery even exceeding that of its female parent 'Green Cloud'. Eight thousand #5 pots planted in the nursery during the wettest summer in memory resulted in zero losses. *Leucophyllum* hybrid 'Purple Rain' is cold hardy to at least 10° F., USDA hardiness zone 8.

COMPARISONS TO RELATED *LEUCOPHYLLUMS*

Compared to its female parent, *Leucophyllum frutescens* 'Green Cloud' (not patented), *Leucophyllum* hybrid 'Purple Rain' is broader relative to height, has a different flower color and its flowers are fragrant while those of 'Green Cloud' are not.

Compared to its male parent, *Leucophyllum laevigatum* (proprietary, not patented), *Leucophyllum* hybrid 'Purple Rain' is a more vigorous, larger plant with a different flower color and has dark green as opposed to yellow green leaves in *Leucophyllum laevigatum*. *Leucophyllum laevigatum* is highly susceptible to damping off diseases in the nursery and is generally considered uneconomic to grow commercially while 'Purple Rain' is highly resistant to damping off diseases.

Compared to *Leucophyllum frutescens* 'San Antonio Rose' (U.S. Plant Pat. No. 33,454), *Leucophyllum* hybrid 'Purple Rain' is a larger plant with a higher width to height ratio than 'San Antonio Rose'. 'San Antonio Rose' has larger flowers of a different color (petal lobes colored 75B abaxially and 75A adaxially) and has silvery leaves compared to dark green leaves for *Leucophyllum* hybrid 'Purple Rain'.

Compared to *Leucophyllum frutescens* 'Convent' (not patented), *Leucophyllum* hybrid 'Purple Rain' is a much larger plant of broader growth form with dark green leaves instead of the silver leaves of 'Convent'. The flowers of 'Convent' are also very different in color (petals colored N74A). 'Convent' is highly susceptible to damping off diseases and as a result is rarely seen in the trade, while *Leucophyllum* hybrid 'Purple Rain' is highly resistant to damping off diseases.

Compared to *Leucophyllum frutescens* 'Compacta' (not patented), *Leucophyllum* hybrid 'Purple Rain' has dark green leaves and fragrant flowers while 'Compacta' has silvery leaves and flowers without fragrance. The flower colors also differ, as those of 'Compacta' have petals colored 75A adaxially.

Compared to *Leucophyllum frutescens* 'White Cloud' (not patented), *Leucophyllum* hybrid 'Purple Rain' has a broad form while 'White Cloud' is upright. 'White Cloud' has white flowers while *Leucophyllum* hybrid 'Purple Rain' has colored flowers, the petals predominantly N78C on the adaxial surface.

Compared to the superficially similar *Leucophyllum frutescens* X *laevigatum* 'Heavenly Cloud' (not, patented) with similar parentage, *Leucophyllum* hybrid 'Purple Rain' has a denser growth form requiring less training pruning than 'Heavenly Cloud'. 'Purple Rain' has improved resistance to damping off diseases compared to 'Heavenly Cloud' as well as more fragrant flowers.

We claim:

1. A new and distinct *Leucophyllum* hybrid plant named 'Purple Rain' substantially as described and illustrated herein.

* * * * *